(12) United States Patent
Boderke

(10) Patent No.: US 7,205,276 B2
(45) Date of Patent: Apr. 17, 2007

(54) ZINC-FREE AND LOW-ZINC INSULIN PREPARATIONS HAVING IMPROVED STABILITY

(75) Inventor: Peter Boderke, Frankfurt am Main (DE)

(73) Assignee: Sanofi-Aventis Deutschland Gmb, Frankfurt am Main (DE)

(*) Notice: Subject to any disclaimer, the term of this patent is extended or adjusted under 35 U.S.C. 154(b) by 0 days.

(21) Appl. No.: 11/007,154

(22) Filed: Dec. 9, 2004

(65) Prior Publication Data

US 2005/0187142 A1    Aug. 25, 2005

Related U.S. Application Data

(62) Division of application No. 10/102,862, filed on Mar. 22, 2002, now Pat. No. 6,960,561.

(30) Foreign Application Priority Data

Mar. 23, 2001  (DE) ............................. 101 14 178

(51) Int. Cl.
 A61K 38/28  (2006.01)
 A61K 38/00  (2006.01)

(52) U.S. Cl. .............................. 514/3; 514/2

(58) Field of Classification Search ............... None
See application file for complete search history.

(56) References Cited

U.S. PATENT DOCUMENTS

| | | | |
|---|---|---|---|
| 4,153,689 A * | 5/1979 | Hirai et al. ............ | 514/3 |
| 5,474,978 A | 12/1995 | Bakaysa et al. | |
| 5,506,203 A | 4/1996 | Bäckström et al. | |
| 5,948,751 A | 9/1999 | Kimer et al. | |
| 6,211,144 B1 * | 4/2001 | Havelund ............ | 514/4 |
| 6,908,897 B2 * | 6/2005 | Brandenburg et al. ....... | 514/3 |
| 2002/0198140 A1 * | 12/2002 | Havelund ............ | 514/3 |

FOREIGN PATENT DOCUMENTS

| | | |
|---|---|---|
| EP | 0 166 529 A1 | 1/1986 |
| EP | 0 200 383 A2 | 12/1986 |
| EP | 0 200 383 A3 | 12/1986 |
| EP | 0 214 826 B1 | 3/1987 |
| EP | 0 375 437 B1 | 6/1990 |
| EP | 0 419 504 B1 | 4/1991 |
| EP | 0 678 522 A1 | 10/1995 |
| WO | WO 92/00321 | 1/1992 |
| WO | WO 98/42749 | 10/1998 |
| WO | WO 98/56406 | 12/1998 |
| WO | WO 00/74736 A1 | 12/2000 |

OTHER PUBLICATIONS

Hinds et al., Bioconjugate Chem. 2000, vol. 11, pp. 195-201.*
W.D. Lougheed et al., "Physical Stability of Insulin Formulations," Diabetes, 32: 424-32 (1983).
H. Thurow and K. Geisen, "Stabilisation of dissolved proteins against denaturation at hydrophobic Interfaces," Diabetologia, 27: 212-18 (1984).
J. Brange and L. Langkjeer, "Chemical stability of insulin 3. Influence of excipients, formulation, and pH," Acta Pharma. Nord. 4(3):149-58 (1992).
D.L. Bakaysa et al., "Physicochemical basis for the rapid time-action of Lys$^{B28}$Pro$^{B29}$-insulin: Dissociation of a protein-ligand complex," Protein Science 5:2521-31 (1996).
J. Brange et al., "Monomeric insulins and their experimental and clinical implications," Diabetes Care 13(9):923-45 (1990).
J. Brange et al., "Neutral insulin solutions physically stabilized by addition of Zn2+," Diabetic Medicine 3:532-6 (1986).
The Diabetes Control and Complications Trial Research Group "The Effect of Intensive Treatment of Diabetes on the Development and Progression of Long-term Complications in Insulin-dependent Diabetes Mellitus," New England Journal of Medicine, 329(14):977-86 (1993).

\* cited by examiner

*Primary Examiner*—B. Dell Chism
(74) *Attorney, Agent, or Firm*—Finnegan, Henderson, Farabow, Garrett & Dunner, LLP

(57) ABSTRACT

The invention relates to a formulation comprising a polypeptide selected from at least one of insulin, an insulin metabolite, an insulin analog, and an insulin derivative; at least one surfactant; optionally at least one preservative; and optionally at least one of an isotonicizing agent, a buffer or an excipient, wherein the formulation is free from or low in zinc. The invention also relates to the production of such insulin preparations and their use as pharmaceutical formulations.

58 Claims, No Drawings

ZINC-FREE AND LOW-ZINC INSULIN PREPARATIONS HAVING IMPROVED STABILITY

This application is a division of application Ser. No. 10/102,862, filed Mar. 22, 2002, now U.S. Pat. No. 6,960,561, and claims priority to German Application No. 101 14 178.5, filed Mar. 23, 2001, each of which are incorporated by reference herein.

The invention relates to stabilized pharmaceutical formulations comprising a polypeptide selected from at least one of insulin (e.g. human insulin, bovine insulin, or porcine insulin, or another animal insulin), an insulin analog, an insulin derivative, and active insulin metabolites, or combinations thereof; at least one surfactant, or combinations of a number of surfactants; optionally at least one preservative, or combinations of a number of preservatives; and optionally at least one of an isotonicizing agent, a buffer or an excipient, or combinations thereof, wherein the pharmaceutical formulation is low in zinc or free from zinc. These formulations can be employed as pharmaceutical or other medicinal formulations, for example, for the treatment of diabetes. They are particularly employable for use in insulin pumps, pens, injectors, inhalers, or for any use in which increased physical stability of the preparation is necessary. The invention likewise relates to parenteral preparations which contain such formulations and can be used in diabetes. The invention also relates to methods for producing the preparations and to methods for improving the stability of insulin preparations.

Worldwide, approximately 120 million people suffer from diabetes mellitus. Among these, approximately 12 million are type I diabetics, for whom the substitution of the lacking endocrine insulin secretion is the only currently possible therapy. The affected persons are dependent lifelong on insulin injections, as a rule a number of times daily. In contrast to type I diabetes, there is not basically a deficiency of insulin in type II diabetes, but in a large number of cases, especially in the advanced stage, treatment with insulin, optionally in combination with an oral antidiabetic, is regarded as the most favorable form of therapy.

In the healthy person, the release of insulin by the pancreas is strictly coupled to the concentration of the blood glucose. Elevated blood glucose levels, such as occur after meals, are rapidly compensated by a corresponding increase in insulin secretion. In the fasting state, the plasma insulin level falls to a basal value which is adequate to guarantee a continuous supply of insulin-sensitive organs and tissue with glucose and to keep hepatic glucose production low in the night. The replacement of the endogenous insulin secretion by exogenous, mostly subcutaneous administration of insulin as a rule does not approximately achieve the quality of the physiological regulation of the blood glucose described above. Often, deviations of the blood glucose upward or downward occur, which in their severest forms can be life-threatening. In addition, however, blood glucose levels which are increased for years without initial symptoms are a considerable health risk. The large-scale DCCT study in the USA (The Diabetes Control and Complications Trial Research Group (1993) N. Engl. J. Med. 329, 977–986) demonstrated clearly that chronically elevated blood glucose levels are essentially responsible for the development of diabetic late damage. Diabetic late damage is microvascular and macrovascular damage which is manifested, under certain circumstances, as retinopathy, nephropathy or neuropathy and leads to loss of sight, kidney failure and the loss of extremities and is moreover accompanied by an increased risk of cardiovascular diseases. It is to be derived from this that an improved therapy of diabetes is primarily to be aimed at keeping the blood glucose as closely as possible in the physiological range. According to the concept of intensified insulin therapy, this should be achieved by repeated daily injections of rapid- and slow-acting insulin preparations. Rapid-acting formulations are given at meals in order to level out the postprandial increase in the blood glucose. Slow-acting basal insulins should ensure the basic supply with insulin, in particular during the night, without leading to hypoglycemia.

Insulin is a polypeptide of 51 amino acids, which are divided into 2 amino acid chains: the A chain having 21 amino acids and the B chain having 30 amino acids. The chains are connected to one another by means of 2 disulfide bridges. Insulin preparations have been employed for diabetes therapy for many years. Not only naturally occurring insulins are used here, but recently also insulin derivatives and analogs.

Insulin analogs are analogs of naturally occurring insulins, namely human insulin or animal insulins, which differ by substitution of at least one naturally occurring amino acid residue with other amino acid residues and/or addition/removal of at least one amino acid residue from the corresponding, otherwise identical, naturally occurring insulin. The added and/or replaced amino acid residues can also be those which do not occur naturally.

Insulin derivatives are derivatives of naturally occurring insulin or of an insulin analog which are obtained by chemical modification. The chemical modification can consist, for example, in the addition, substitution or deletion of one or more specific chemical groups to one or more amino acids. It can also involve the addition, substitution or deletion of one or more chemical groups of the peptide backbone, such as, at the amino and/or carboxyl terminus.

Active insulin metabolites of naturally occurring insulin, of insulin analogs, or of insulin derivatives may be formed in the formulations of the invention by chemical, enzymatic, or oxidative means. Active insulin metabolites retain at least partial insulin activity. Examples are products of chemical or oxidative degradation of insulin polypeptides.

As a rule, insulin derivatives and insulin analogs have a somewhat modified action compared with human insulin.

Insulin analogs having an accelerated onset of action are described in EP 0 214 826, EP 0 375 437 and EP 0 678 522. EP 0 124 826 relates, inter alia, to substitutions of B27 and B28. EP 0 678 522 describes insulin analogs which have various amino acids, preferably proline, in position B29, but not glutamic acid.

EP 0 375 437 includes insulin analogs with lysine or arginine in B28, which can optionally additionally be modified in B3 and/or A21.

In EP 0 419 504, insulin analogs are disclosed which are protected against chemical modifications, in which asparagine in B3 and at least one further amino acid in the positions A5, A15, A18 or A21 are modified.

In WO 92/00321, insulin analogs are described in which at least one amino acid of the positions B1–B6 is replaced by lysine or arginine. According to WO 92/00321, insulins of this type have a prolonged action.

The insulin preparations of naturally occurring insulins on the market for insulin substitution differ in the origin of the insulin (e.g. bovine, porcine, human insulin, or another mammalian or animal insulin), and also the composition, whereby the profile of action (onset of action and duration of action) can be influenced. By combination of various insulin preparations, very different profiles of action can be obtained and blood sugar values which are as physiological as possible can be established. Preparations of naturally occurring insulins, as well as preparations of insulin derivatives or insulin analogs which show modified kinetics, have been on the market for some time. Recombinant DNA technology today makes possible the preparation of such modified insulins. These include "monomeric insulin analogs" such as insulin Lispro, insulin Aspart, and HMR 1964 (Lys(B3), Glu(B29) human insulin), all of which have a rapid onset of action, as well as insulin Glargin, which has a prolonged duration of action.

In addition to the duration of action, the stability of the preparation is very important for patients. Stabilized insulin formulations having increased physical long-term stability are needed in particular for preparations which are exposed to particular mechanical stresses or relatively high temperatures. These include, for example, insulins in administration systems such as pens, inhalation systems, needleless injection systems or insulin pumps. Insulin pumps are either worn on or implanted in the body of the patient. In both cases, the preparation is exposed to the heat of the body and movement and to the delivery motion of the pump and thus to a very high thermomechanical stress. Since insulin pens too (disposable and reutilizable pens) are usually worn on the body, the same applies here. Previous preparations have only a limited stability under these conditions.

Insulin is generally present in neutral solution in pharmaceutical concentration in the form of stabilized zinc-containing hexamers, which are composed of 3 identical dimer units (Brange et al., Diabetes Care 13:923–954 (1990)). However, the profile of action an insulin preparation may be improved by reducing the oligomeric state of the insulin it contains. By modification of the amino acid sequence, the self-association of insulin can be decreased. Thus, the insulin analog Lispro, for example, mainly exists as a monomer and is thereby absorbed more rapidly and shows a shorter duration of action (H P T Ammon and C. Werning; Antidiabetika [Antidiabetics]; 2. Ed.; Wiss. Verl.-Ges. Stuttgart; 2000; p. 94.f). However, the rapid-acting insulin analogs which often exist in the monomeric or dimeric form are less stable and more prone to aggregate under thermal and mechanical stress than hexameric insulin. This makes itself noticeable in cloudiness and precipitates of insoluble aggregates. (Bakaysa et al, U.S. Pat. No. 5,474,978). These higher molecular weight transformation products (dimers, trimers, polymers) and aggregates decrease not only the dose of insulin administered but can also induce irritation or immune reactions in patients. Moreover, such insoluble aggregates can affect and block the cannulas and tubing of the pumps or needles of pens. Since zinc leads to an additional stabilization of insulin through the formation of zinc-containing hexamers, zinc-free or low-zinc preparations of insulin and insulin analogs are particularly susceptible to instability. In particular, monomeric insulin analogs having a rapid onset of action are prone to aggregate and become physically unstable very rapidly, because the formation of insoluble aggregates proceeds via monomers of insulin.

In order to guarantee the quality of an insulin preparation, it is necessary to avoid the formation of aggregates. There are various approaches for stabilizing insulin formulations. Thus, in international patent application WO98/56406, formulations stabilized by TRIS or arginine buffer have been described. U.S. Pat. No. 5,866,538 describes an insulin preparation which contains glycerol and sodium chloride in concentrations of 5–100 mM and should have an increased stability. U.S. Pat. No. 5,948,751 describes insulin preparations having increased physical stability, which is achieved by addition of mannitol or similar sugars. The addition of excess zinc to a zinc-containing insulin solution can likewise increase the stability (J. Brange et al., Diabetic Medicine, 3: 532–536, 1986). The influence of the pH and various excipients on the stability of insulin preparations has also been described in detail (J. Brange & L. Langkjaer, Acta Pharm. Nordica 4: 149–158).

Often, these stabilization methods are not adequate for increased demands (improvement in ability to be kept at room or body temperature and under mechanical stress) or for "monomeric" insulin analogs or rapid-acting insulins, which are particularly susceptible to physical stress. Moreover, all commercial insulin preparations contain zinc, which is added to stabilize the preparation. Thus, Bakaysa et al. in U.S. Pat. No. 5,474,978 describe stabilized formulations of insulin complexes which consist of 6 insulin analog monomers, 2 zinc atoms and at least 3 molecules of a phenolic preservative. These formulations can additionally contain a physiologically acceptable buffer and a preservative. If it is wished, however, to prepare zinc-free or low-zinc insulin preparations, the stabilization methods mentioned are not adequate for a marketable preparation. For example, it was not possible to develop a zinc-free preparation of insulin Lispro on account of inadequate physical stability (Bakaysa et al., Protein Science (1996), 5:2521–2531). Low-zinc or zinc-free insulin formulations having adequate stability, in particular physical stability, are not described in the prior art.

The present invention was thus based on the object of finding zinc-free preparations for insulins and their derivatives and analogs, which are distinguished by a high stability.

It has now surprisingly been found that the addition of surfactants (emulsifiers) such as, for example, poloxamers or polysorbates (such as polyoxyethylenesorbitan monolaurate (TWEEN® 20) can drastically increase the stability of insulin preparations. Thus, even zinc-free preparations can be prepared which have a superior stability, and which are capable of being used in infusion pumps or other administration systems. These preparations show increased stability, particularly under stress conditions. This finding applies to insulin, insulin analogs, and insulin derivatives, as well as to mixtures of insulin, insulin analogs, and insulin derivatives.

In neutral preparations, insulin forms complexes with zinc ions. Here, at an adequate zinc concentration, stable hexamers are formed from 6 insulin molecules and 2 zinc ions. For the formation of this structure, a zinc concentration of at least 0.4% (w/w) relative to the insulin is necessary. This corresponds in the case of a preparation of 100 IU/ml of insulin to a concentration of about 13 µg/ml of zinc. An excess of zinc (e.g. 4 zinc ions per hexamer) again markedly stabilizes the preparation against physical stress (J. Brange et al., Neutral insulin solutions physically stabilized by the addition of $Zn^{2+}$. Diabetic Med. 3, 532–536 (1986)). In contrast to this, in preparations having lower zinc concentrations (<0.4 percent by weight based on insulin), the formation of the hexamers is reduced. This leads to a dramatically reduced stability of the preparation (J. Brange and L. Langkjaer; Acta Pharm Nord, 4: 149–158 (1992)). "Zinc-free" or "low-zinc" within the meaning of this application therefore means the presence of less than 0.4 percent by weight of zinc based on the insulin content of the preparation, for example, less than 0.2 percent by weight based on the insulin content. For a customary insulin preparation containing 100 units per milliliter (0.6 µmol/ml), this means, for example, a concentration of less than 13 µg/ml of Zn$^{++}$ ions (0.2 μmol/ml), for example, less than 6.5 μg/ml of Zn$^{++}$ ions, in the pharmaceutical preparation, based on an insulin concentration of 100 units/ml. The freedom from zinc can also be achieved by addition of zinc-complexing substances, such as, for example, citrate or EDTA, so that sufficient zinc ions are not available for the formation of the insulin/zinc hexamer complex.

The pharmaceutical preparations contain about 60–6000 nmol/ml, for example, about 240–3000 nmol/ml, of an insulin, an active insulin metabolite, an insulin analog or an insulin derivative.

Surfactants which can be used are, inter alia, nonionic or ionic (anionic, cationic or amphoteric) surfactants. Pharmaceutically customary surfactants may be used, such as: alkali metal soaps, amine soaps and alkaline earth metal soaps (for example, stearates, palmitates, oleates, and ricinoleates), alkylsulfates and alkylsulfonates (for example, sodium laurylsulfate, sodium cetylsulfate, and sodium stearylsulfate), natural surfactants (such as, bile acid salts, saponins, and gum arabic), cationic surfactants (such as, alkonium bromides, cetylpyridinium chloride, and cetrimide), fatty alcohols (for example, cetyl alcohol, stearyl alcohol, and cholesterol), esters, such as fatty acid esters, and ethers of polyhydric alcohols (e.g. esters or ethers of glycerol, sorbitol, polyethylene glycol and the like (e.g. SPAN®, TWEEN®, MYRJ®, BRIJ®, and CREMOPHOR®), and polyols (e.g. poloxamers).

The surfactants may be present in the pharmaceutical composition in a concentration of about 0.1 μg/ml–10000 μg/ml, for example, about 1 μg/ml–1000 μg/ml.

The preparation can additionally contain preservatives (e.g. phenol, cresol, and parabens), isotonicizing agents (e.g. mannitol, sorbitol, lactose, dextrose, trehalose, sodium chloride, and glycerol), buffer substances, salts, acids and alkalis, and further excipients. These substances can in each case be present individually or alternatively as mixtures.

Glycerol, dextrose, lactose, sorbitol and mannitol are customarily present in the pharmaceutical preparation in a concentration of about 100–250 mM. NaCl may be present in a concentration of up to about 150 mM. Buffer substances, such as, for example, phosphate, acetate, citrate, arginine, glycylglycine or TRIS (i.e. 2-amino-2-hydroxymethyl-1,3-propanediol) buffer and corresponding salts, may be present in a concentration of about 5–250 mM, generally about 10–100 mM. Further excipients can, inter alia, be salts, arginine, protamine, or SURFEN® (also referred to herein as amino quinurid (INN), or 1,3-bis(4-amino-2-methyl-6-chinolyl) urea).

The invention therefore relates to a formulation comprising a polypeptide selected from at least one of insulin, an insulin analog, an insulin derivative, and an active insulin metabolite; at least one surfactant; optionally at least one preservative; and optionally at least one of an isotonicizing agent, buffer substances and/or further excipients. The formulation is either free from or low in zinc.

In one embodiment, the surfactant is selected from at least one of alkali metal soaps, amine soaps, alkaline earth metal soaps, alkylsulfates, alkylsulfonates, natural surfactants, cationic surfactants, fatty alcohols, partial and fatty acid esters of polyhydric alcohols (such as of glycerol and sorbitol), ethers of polyhydric alcohols, polyethylene glycol ethers, and polyols.

In some embodiments, the alkali metal, amine, and alkaline earth metal soaps mentioned are selected from at least one of stearates, palmitates, oleates, and ricinoleates. In some embodiments, the alkylsulfates are selected from at least one of sodium laurylsulfate, sodium cetylsulfate, and sodium stearylsulfate.

In some embodiments, the natural surfactants are selected from at least one of bile acid salts, saponins, gum arabic, and lecithins. The cationic surfactants may be selected from at least one of alkonium bromides, cetylpyridinium chloride, and CETRIMIDE® (an alkyltrimethylammonium bromide).

In some embodiments, the fatty alcohols are selected from at least one of cetyl alcohol, stearyl alcohol, and cholesterol.

In some embodiments, esters and ethers of polyhydric alcohols such as glycerol, polyethylene glycol, sucrose, and sorbitol are selected as surfactants. The esters and ethers of polyhydric alcohols include fatty acid esters and ethers. The esters and ethers may also be partial esters and ethers, in which only some hydroxyl groups are modified to the ester or ether form, or they may be complete esters or ethers, in which all hydroxyl groups are modified. Examples of esters and ethers of polyhydric alcohols that may be employed in this invention include SPAN® (fatty acid esters of sorbitan), TWEEN® (polysorbates, fatty acid esters of polyoxyethylenesorbitan), MYRJ® (polyoxyethylene stearates), BRIJ® (polyoxyethylene ethers), and/or CREMOPHOR® (polyoxyethylene fatty acid esters), each of which are commercially available, and may be employed, in a variety of molecular weights.

In some embodiments, the surfactant may be a polyol. Example polyols are polypropylene glycols, polyethylene glycols, poloxamers, Pluronics, and Tetronics.

The preservative, in some embodiments, is selected from at least one of phenol, cresol, and parabens.

In some embodiments, the isotonicizing agent is selected from at least one of mannitol, sorbitol, sodium chloride, and glycerol. The excipients, in some embodiments, are selected from buffer substances, acids, alkalis, salts, protamine, arginine, and SURFEN®.

In some embodiments, the polypeptide of the preparation is an insulin occurring in nature, for example human, bovine or porcine insulin, or the insulin of another animal or mammal. In some embodiments, the polypeptide of the preparation comprises an insulin analog, selected from at least one of Gly(A21)-Arg(B31)-Arg(B32) human insulin; Lys(B3)-Glu(B29) human insulin; Lys$^{B28}$Pro$^{B29}$ human insulin, B28 Asp human insulin, human insulin, in which proline in position B28 has been substituted by Asp, Lys, Leu, Val or Ala and where in position B29 Lys can be substituted by Pro; AlaB26 human insulin; des(B28-B30) human insulin; des(B27) human insulin or des(B30) human insulin. In additional embodiments, the polypeptide of the preparation comprises an insulin derivative selected from at least one of B29-N-myristoyl-des(B30) human insulin, B29-N-palmitoyl-des(B30) human insulin, B29-N-myristoyl human insulin, B29-N-palmitoyl human insulin, B28-N-myristoyl Lys$^{B28}$Pro$^{B29}$ human insulin, B28-N-palmitoyl-Lys$^{B28}$Pro$^{B29}$ human insulin, B30-N-myristoyl-Thr$^{B29}$Lys$^{B30}$ human insulin, B30-N-palmitoyl-Thr$^{B29}$Lys$^{B30}$ human insulin, B29-N-(N-palmitoyl-γ-glutamyl)-des(B30) human insulin, B29-N-(N-lithocholyl-γ-glutamyl)-des(B30) human insulin, B29-N-(ω-carboxyheptadecanoyl)-des(B30) human insulin, and B29-N-(ω-carboxyheptadecanoyl) human insulin. In some embodiments, the polypeptide may comprise an active insulin metabolite. Some embodiments comprise preparations containing mixtures of one or more of an insulin, an insulin analog, an insulin derivative, and an active insulin metabolite, for example, selected from those described above.

The invention further relates to a pharmaceutical formulation as described above, in which the insulin, the insulin analog, the active insulin metabolite and/or the insulin derivative is present in a concentration of 60–6000 nmol/ml, such as a concentration of 240–3000 nmol/ml (which corresponds approximately to a concentration of 1.4–35 mg/ml or 40–500 units/ml). The surfactant may be present in a concentration of 0.1–10000 µg/ml, such as a concentration of 1–1000 µg/ml.

The invention further relates to a pharmaceutical formulation as mentioned above, in which glycerol and/or mannitol is present in a concentration of 100–250 mM, and/or chloride is present in a concentration of up to 150 mM.

The invention further relates to a pharmaceutical formulation as mentioned above, in which a buffer substance is present in a concentration of 5–250 mM.

The invention further relates to a pharmaceutical insulin formulation which contains further additives such as, for example, salts, protamine, or SURFEN®, which delay the release of insulin. Mixtures of such delayed-release insulins with formulations as described above are also included herein.

The invention further relates to a method for the preparation of such pharmaceutical formulations. For example, the components may be mixed together in the form of aqueous solutions, after which the pH is adjusted to a desired level, and the mixture is made up to the final volume with water. In some embodiments, after the mixture is made up to the final volume with water the mixture may comprise 1–5 mg/ml of cresol, for example, about 3 mg/ml, or about 3.15 mg/ml; 1.4–35 mg/ml of insulin, an insulin analog, an insulin derivative, and/or an active insulin metabolite, such as, 3–5 mg/ml, 3–4 mg/ml, or about 3.5 mg/ml; about 1–10 mg/ml of trometamol, for example, about 5–7 mg/ml, or about 6.0 mg/ml of trometamol; 1–8 mg/ml of NaCl, such as, about 4–6 mg/ml, or about 5.0 mg/ml of NaCl; and 1–1000 µg/ml of TWEEN® 20, for example, about 10–100 µg/ml, or about 100 µg/ml (0.1 mg/ml) of TWEEN® 20. In some embodiments, the polypeptide present in this final mixture comprises Lys(B3), Glu(B29) human insulin (HMR 1964).

The invention further likewise relates to the administration of such formulations for the treatment of diabetes mellitus. The formulations may be administered to mammalian patients, such as humans and domestic mammals.

The invention further relates to the use or the addition of surfactants as stabilizer during the process for the preparation of insulin, insulin analogs or insulin derivatives or their preparations.

In the pharmaceutical formulations described, the polypeptide is selected from insulin, an insulin analog, an insulin derivative, and/or an active insulin metabolite, the pH is between 2 and 12, generally between 6 and 8.5, and often between 7 and 7.8.

The application is described below with the aid of some examples, which should in no case act in a restrictive manner.

EXAMPLES

Comparison investigations: Various zinc-free preparations containing the insulin analog HMR1964 (Lys(B3), Glu(B29), human insulin) were prepared. To this end, zinc-free HMR1964 and the other constituents were dissolved in one part of water for injection purposes and the pH was adjusted to 7.3+/−0.2 with hydrochloric acid/NaOH and made up to the final volume. The concentration of HMR 1964 in each of the experiments described below was 3.5 mg/ml (corresponds to 100 units/ml). A second preparation was prepared identically, but a specific amount of a surfactant was additionally added. The solutions were dispensed into 5 ml or 10 ml glass vessels (vials) and fitted with crimp caps. These vessels were then exposed to the following stress conditions.

1. Rotation test: In each case 5 vessels of a batch and 5 vessels of the comparison batch were subjected to a rotation test. To this end, the vessels were mounted in a rotator and rotated top over bottom (360°) at 37° C. at 60 rpm. After defined times, the turbidity of the preparations situated in the vessels was compared with turbidity standards or determined in formazine nephelometric units (FNU) using a laboratory turbidity photometer (nephelometer). The experiment was carried out until a turbidity value of 18 FNU was exceeded in all vessels.

2. Shaking test: The vessels were placed on a laboratory shaker in an incubator and shaken at 30° C. at 100 movements/min. After defined times, the turbidity value of the samples was determined by means of a laboratory turbidity photometer (nephelometer) in formazine nephelometric units (FNU).

Example 1

Stabilization of HMR1964 by Addition of Zinc in the Rotation Test a) Zinc-free HMR1964 (calculated such that a concentration of 3.5 mg/ml results in the finished formulation) was dissolved in an aqueous solution, which in the final formulation contained 2.7 mg/ml of m-cresol, 20 mg/ml of glycerol and 6 mg/ml of trometamol (tris), and the pH was adjusted to 7.2–7.4 (measured at room temperature) using 1 N hydrochloric acid/1 N NaOH. The solution was made up to the final volume with water and sterile-filtered through a 0.2 µm filter. It was then filled into 5 ml injection vials and sealed using caps.

b) A comparison solution was prepared identically, but before making up with water a corresponding amount of a 0.1% strength zinc chloride stock solution was added, so that a zinc content of 15 µg/ml results in the finished formulation.

In each case, 5 samples were then stressed in the rotation test and the turbidity was determined after various periods of time. The results are shown in the following table.

| Description | Number of test samples with turbidity > 18 FNU after: | | | | | |
|---|---|---|---|---|---|---|
| | 0 h | 8 h | 16 h | 32 h | 40 h | 56 h |
| HMR1964 without addition | 0 | 5 | — | — | — | — |
| HMR1964 + 15 µg/ml of Zn | 0 | 0 | 0 | 0 | 4 | 5 |

The addition of zinc markedly delayed the resulting turbidity of the solution in terms of time and thereby stabilized the HMR1964 formulation. Without addition of zinc, the preparation had a marked turbidity in the rotation test even after 8 hours.

Example 2

Stabilization of HMR1964 by Addition of Polysorbate 20 (TWEEN® 20) in the Rotation Test a) Zinc-free HMR1964 (calculated such that a concentration of 3.5 mg/ml results in the finished formulation) was dissolved in an aqueous solution which contained 3.15 mg/ml of m-cresol, 5 mg/ml of NaCl and 6 mg/ml of trometamol in the final formulation and the pH was adjusted to 7.2–7.4 (measured at room temperature) using 1 N hydrochloric acid/1 N NaOH. The solution was made up to the final volume with water and sterile-filtered through a 0.2 µm filter. It was then filled into 5 ml injection vials and sealed using caps.

b) A comparison solution was prepared identically, but before making up with water a corresponding amount of a 0.1% strength polysorbate 20 (TWEEN® 20) stock solution was added, so that a concentration of 10 µg/ml results in the finished formulation.

In each case 5 samples were then stressed in the rotation test and the turbidity was determined after various periods of time. The results are shown in the following table.

| Description | Number of test samples with turbidity > 18 FNU after: | | | | | |
|---|---|---|---|---|---|---|
| | 0 h | 8 h | 16 h | 24 h | 32 h | 40 h |
| HMR1964 without addition | 0 | 5 | — | — | — | — |
| HMR1964 + 10 µg/ml of TWEEN ® 20 | 0 | 0 | 0 | 0 | 5 | — |

The addition of polysorbate 20 delayed the occurrence of turbidity very markedly.

Example 3

Stabilization of HMR1964 by Addition of Poloxamer in the Rotation Test a) Zinc-free HMR1964 (calculated such that a concentration of 3.5 mg/ml results in the finished formulation) was dissolved in an aqueous solution which contained 4.5 mg/ml of phenol, 5 mg/ml of NaCl and 6 mg/ml of trometamol in the final formulation and the pH was adjusted to 7.2–7.4 (measured at room temperature) using 1 N hydrochloric acid/1 N NaOH. The solution was made up to the final volume with water and sterile-filtered through a 0.2 µm filter. It was then filled into 5 ml injection vials and sealed using caps.

b) A comparison solution was prepared identically, but before making up with water a corresponding amount of a 0.1% strength poloxamer 171 (e.g. GENAPOL®) stock solution was added, such that a concentration of 10 µg/ml results in the finished formulation.

In each case 5 samples were then stressed in the rotation test and the turbidity was determined after various periods of time. The results are shown in the following table.

| Description | Number of test samples with turbidity > 18 FNU after: | | | | | |
|---|---|---|---|---|---|---|
| | 0 h | 8 h | 16 h | 24 h | 32 h | 40 h |
| HMR1964 without addition | 0 | 5 | — | — | — | — |
| HMR1964 + 0.01 µg/ml of poloxamer 171 | 0 | 0 | 0 | 2 | 5 | — |

The addition of poloxamer 171 also delayed the occurrence of turbidity markedly and stabilizes the preparation.

Example 4

Stabilization of HMR1964 by Addition of Polysorbate 20 or Polysorbate 80 in the Shaking Test a) Zinc-free HMR1964 (calculated such that a concentration of 3.5 mg/ml results in the finished formulation) was dissolved in an aqueous solution which contained 3.15 mg/ml of m-cresol, 5 mg/ml of NaCl and 6 mg/ml of trometamol in the final formulation and the pH was adjusted to 7.2–7.4 (measured at room temperature) using 1 N hydrochloric acid/1 N NaOH. The solution was made up to the final volume with water and sterile-filtered through a 0.2 µm filter. It was then filled into 5 ml injection vials and sealed using caps.

b) A comparison solution was prepared identically, but before making up with water a corresponding amount of a 0.1% strength polysorbate 20 (TWEEN® 20) stock solution was added, such that a concentration of 10 µg/ml results in the finished formulation.

c) A further comparison solution was prepared identically as in b), but this time polysorbate 80 (TWEEN® 80) was used instead of polysorbate 20.

The samples were shaken at 30° C. on a laboratory shaker (60 rpm) and the turbidity of the samples was measured after specific times. The results are shown in the following table.

| Addition | Shaking test, turbidity (FNU) after | | | | |
|---|---|---|---|---|---|
| | Start | 1 week | 2 weeks | 3 weeks | 4 weeks |
| Without addition | 0.55 | 2.04 | 4.86 | 6.12 | 10.51 |
| 0.01 mg/ml of Tween 20 | 1.75 | 2.60 | 2.44 | 2.44 | 3.80 |
| 0.01 mg/ml of Tween 80 | 2.38 | 2.98 | 2.86 | 3.01 | 4.14 |

Both the addition of polysorbate 20 and of polysorbate 80 had a stabilizing effect on HMR1964 in the shaking test.

Example 5

Stabilization of HMR1964 by Addition of Zinc or Poloxamer (GENAPOL®) in the Shaking Test a) Zinc-free HMR1964 (calculated such that a concentration of 3.5 mg/ml results in the finished formulation) was dissolved in an aqueous solution which contained 3.3 mg/ml of phenol, 5 mg/ml of NaCl and 6 mg/ml of trometamol in the final formulation and the pH was adjusted to 7.2–7.4 (measured at room temperature) using 1 N hydrochloric acid/1 N NaOH. The solution was made up to the final volume with water and sterile-filtered through a 0.2 µm filter. It was then filled into 5 ml injection vials and sealed using caps.

b) A comparison solution was prepared identically, but before making up with water a corresponding amount of a 0.1% strength poloxamer 171 (GENAPOL®) stock solution was added, such that a concentration of 10 µg/ml results in the finished formulation.

c) A further comparison solution was prepared as described in a), but instead of poloxamer, a corresponding amount of a 0.1% strength zinc chloride stock solution was added to the solution before making up with water, so that a concentration of 15 µg/ml of zinc results in the finished formulation.

| Addition | Shaking test, turbidity (FNU) after | | | | |
|---|---|---|---|---|---|
| | Start | 1 week | 2 weeks | 3 weeks | 4 weeks |
| None | 0.39 | 0.70 | 4.46 | 8.74 | 14.11 |
| 0.01 mg/ml of poloxamer | 0.36 | 0.57 | 0.52 | 1.59 | 0.89 |
| 0.015 mg/ml of Zn | 1.02 | 0.68 | 0.70 | 0.56 | 0.86 |

Both an addition of zinc and the addition of poloxamer prevented the occurrence of turbidity in the shaking test.

Example 6

Stabilization of HMR1964 by Addition of Poloxamer in the Rotation Test a) Zinc-free HMR1964 (calculated such that a concentration of 3.5 mg/ml results in the finished formulation) was dissolved in an aqueous solution which contained 3.3 mg/ml of phenol, 5 mg/ml of NaCl and 6 mg/ml of trometamol in the final formulation and the pH was adjusted to 7.2–7.4 (measured at room temperature) using 1 N hydrochloric acid/1 N NaOH. The solution was made up to the final volume with water and sterile-filtered through a 0.2 μm filter. It was then filled into 5 ml injection vials and sealed using caps.

b) A comparison solution was prepared identically, but before making up with water a corresponding amount of a 0.1% strength poloxamer 171 (GENAPOL®) stock solution was added, such that a concentration of 100 μg/ml results in the finished formulation.

In each case 5 samples were then stressed in the rotation test and the turbidity was determined after various periods of time. The results are shown in the following table.

| Description | Number of test samples with turbidity > 18 FNU after: | | | | | |
|---|---|---|---|---|---|---|
| | 0 h | 8 h | 16 h | 24 h | 32 h | 40 h |
| HMR1964 without addition | 0 | 5 | — | — | — | — |
| HMR1964 + 0.10 mg/ml of poloxamer 171 | 0 | 0 | 0 | 0 | 1 | 5 |

The addition of 100 μg/ml of poloxamer likewise stabilizes the HMR1964 preparation very markedly.

What is claimed is:

1. An aqueous liquid formulation comprising
   at least one insulin derivative;
   at least one surfactant;
   optionally at least one preservative; and
   optionally at least one of an isotonicizing agent, a buffer, and an excipient, wherein the formulation is stable and free from or contains less than 0.2% by weight of zinc based on the insulin content of the formulation.

2. The formulation as claimed in claim 1, wherein the at least one surfactant is selected from at least one of alkali metal soaps, amine soaps, alkaline earth metal soaps, alkylsulfates, alkylsulfonates, natural surfactants, cationic surfactants, fatty alcohols, fatty acids, esters of polyhydric alcohols, ethers of polyhydric alcohols, and polyols.

3. The formulation as claimed in claim 1, wherein the surfactant comprises a soap selected from at least one of a stearate, a palmitate, an oleate, and a ricinoleate.

4. The formulation as claimed in claim 2, wherein the alkylsulfates are selected from at least one of sodium laurylsulfate, sodium cetylsulfate, and sodium stearylsulfate.

5. The formulation as claimed in claim 2, wherein the natural surfactants are selected from at least one of bile acid salts, saponins, gum arabic, and lecithins.

6. The formulation as claimed in claim 2, wherein the cationic surfactants are selected from at least one of alkonium halides, cetylpyridinium chloride, and alkyltrimethylammonium bromide.

7. The formulation as claimed in claim 2, wherein the fatty alcohols are selected from at least one of cetyl alcohol, stearyl alcohol, and cholesterol.

8. The formulation as claimed in claim 2, wherein the esters of polyhydric alcohols are selected from at least one of esters of sorbitol, glycerol, sucrose, and polyethylene glycol.

9. The formulation as claimed in claim 2, wherein the esters of polyhydric alcohols are fatty acid esters.

10. The formulation as claimed in claim 2, wherein the ethers of polyhydric alcohols are selected from at least one of ethers of sorbitol, glycerol, sucrose, and polyethylene glycol.

11. The formulation as claimed in claim 1, wherein the surfactant comprises at least one of a polysorbate, a sorbitan ester, a polyoxyethylene stearate, a polyoxyethylene ether, and a polyethylene glycol ether.

12. The formulation as claimed in claim 2, wherein the polyols are selected from at least one of polypropylene glycols, polyethylene glycols, poloxamers, Pluronics, and Tetronics.

13. The formulation as claimed in claim 1, wherein the preservative is selected from at least one of phenol, cresol, chlorocresol, benzyl alcohol, and parabens.

14. The formulation as claimed in claim 1, wherein the isotonicizing agent is selected from at least one of mannitol, sorbitol, lactose, dextrose, trehalose, sodium chloride, and glycerol.

15. The formulation as claimed in claim 1, wherein the excipient is selected from at least one of a buffer substance, an acid, an alkali, a salt, protamine, arginine, and amino quinurid.

16. The formulation as claimed in claim 15, wherein the buffer substance is selected from TRIS, phosphate, citrate, acetate, and glycylglycine.

17. The formulation as claimed in claim 1, wherein the at least one insulin derivative is selected from at least one of B29-N-myristoyl-des(B30) human insulin; B29-N-palmitoyl-des(B30) human insulin; B29-N-myristoyl human insulin; B29-N-palmitoyl human insulin; B28-N-myristoyl Lys$^{B28}$Pro$^{B29}$ human insulin; B28-N-palmitoyl-Lys$^{B28}$Pro$^{B29}$ human insulin; B30-N-myristoyl-Thr$^{B29}$Lys$^{B30}$ human insulin; B30-N-palmitoyl-Thr$^{B29}$Lys$^{B30}$ human insulin; B29-N-(N-palmitoyl-γ-glutamyl)-des(B39) human insulin; B29-N-(N-lithocholyl-γ-glutamyl)-des(B30) human insulin; B29-N-(ω-carboxyheptadecanoyl)-des(B30) human insulin; and B29-N-(ω-carboxyheptadecanoyl) human insulin.

18. The formulation as claimed in claim 1, in which the at least one insulin derivative is present in a concentration of 60–6000 nmol/ml.

19. The formulation as claimed in claim 18, wherein the at least one insulin derivative is present in a concentration of 240–3000 nmol/ml.

20. The formulation as claimed in claim 1, in which the at least one surfactant is present in a concentration of 0.1–10000 μg/ml.

21. The formulation as claimed in claim 20, in which the surfactant is present in a concentration of 1–1000 μg/ml.

22. The formulation as claimed in claim 1, in which the surfactant and/or isotonicizing agent comprises at least one of glycerol and mannitol in a concentration of 100–250 mM.

23. The formulation as claimed in claim 22, further comprising chloride as a buffer substance and/or isotonicizing agent in a concentration of up to 150 mM.

24. The formulation as claimed in claim 1, in which a buffer substance is present in a concentration of 5–250 mM.

25. A process for the production of the formulation as claimed in claim 1, wherein the components are mixed together in the form of aqueous solutions, the pH is adjusted to a desired level, and the mixture is made up to the final volume with water.

26. The formulation of claim 1 wherein the surfactant comprises polysorbate 20, and the formulation further comprises cresol, trometamol and NaCl.

27. An aqueous liquid formulation obtainable by the process as claimed in claim 25.

28. A method of treating diabetes mellitus comprising administering the formulation as claimed in claim 1 to a patient in need thereof.

29. The formulation of claim 1 further comprising at least one insulin, insulin derivative, or active insulin metabolite.

30. An aqueous liquid formulation comprising
at least one insulin derivative;
at least one surfactant;
optionally at least one preservative; and
optionally at least one of an isotonicizing agent, a buffer, and an excipient, wherein the formulation is stable and free from zinc or contains less than a 2:6 ratio of zinc to insulin.

31. The formulation as claimed in claim 30, wherein the at least one surfactant is selected from at least one of alkali metal soaps, amine soaps, alkaline earth metal soaps, alkylsulfates, alkylsulfonates, natural surfactants, cationic surfactants, fatty acids, fatty alcohols, esters of polyhydric alcohols, ethers of polyhydric alcohols, and polyols.

32. The formulation as claimed in claim 30, wherein the surfactant comprises a soap selected from at least one of a stearate, a palmitate, an oleate, and a ricinoleate.

33. The formulation as claimed in claim 31, wherein the alkylsulfates are selected from at least one of sodium laurylsulfate, sodium cetylsulfate, and sodium stearylsulfate.

34. The formulation as claimed in claim 31, wherein the natural surfactants are selected from at least one of bile acid salts, saponins, gum arabic, and lecithins.

35. The formulation as claimed in claim 31, wherein the cationic surfactants are selected from at least one of alkonium halides, cetylpyridinium chloride, and alkyltrimethylammonium bromide.

36. The formulation as claimed in claim 31, wherein the fatty alcohols are selected from at least one of cetyl alcohol, stearyl alcohol, and cholesterol.

37. The formulation as claimed in claim 31, wherein the esters of polyhydric alcohols are selected from at least one of esters of sorbitol, glycerol, sucrose, and polyethylene glycol.

38. The formulation as claimed in claim 31, wherein the esters of polyhydric alcohols are fatty acid esters.

39. The formulation as claimed in claim 31, wherein the ethers of polyhydric alcohols are selected from at least one of ethers of sorbitol, glycerol, sucrose, and polyethylene glycol.

40. The formulation as claimed in claim 30, wherein the surfactant comprises at least one of a polysorbate, a sorbitan ester, a polyoxyethylene stearate, a polyoxyethylene ether, and a polyethylene glycol ether.

41. The formulation as claimed in claim 31, wherein the polyols are selected from at least one of polypropylene glycols, polyethylene glycols, poloxamers, Pluronics, and Tetronics.

42. The formulation as claimed in claim 30, wherein the preservative is selected from at least one of phenol, cresol, chlorocresol, benzyl alcohol, and parabens.

43. The formulation as claimed in claim 30, wherein the isotonicizing agent is selected from at least one of mannitol, sorbitol, lactose, dextrose, trehalose, sodium chloride, and glycerol.

44. The formulation as claimed in claim 30, wherein the excipient is selected from at least one of a buffer substance, an acid, an alkali, a salt, protamine, arginine, and amino quinurid.

45. The formulation as claimed in claim 44, wherein the buffer substance is selected from TRIS, phosphate, citrate, acetate, and glycylglycine.

46. The formulation as claimed in claim 30, wherein the at least one insulin derivative is selected from at least one of B29-N-myristoyl-des(B30) human insulin; B29-N-palmitoyl-des(B30) human insulin; B29-N-myristoyl human insulin; B29-N-palmitoyl human insulin; B28-N-myristoyl Lys$^{B28}$Pro$^{B29}$ human insulin; B28-N-palmitoyl-Lys$^{B28}$Pro$^{B29}$ human insulin; B30-N-myristoyl-Thr$^{B29}$Lys$^{B30}$ human insulin; B30-N-palmitoyl-Thr$^{B29}$Lys$^{B30}$ human insulin; B29-N-(N-palmitoyl-γ-glutamyl)-des(B39) human insulin; B29-N-(N-lithocholyl-γ-glutamyl)-des(B30) human insulin; B29-N-(ω-carboxyheptadecanoyl)-des(B30) human insulin; and B29-N-(ω-carboxyheptadecanoyl) human insulin.

47. The formulation as claimed in claim 30, in which the at least one insulin derivative is present in a concentration of 60–6000 nmol/ml.

48. The formulation as claimed in claim 47, wherein the at least one insulin derivative is present in a concentration of 240–3000 nmol/ml.

49. The formulation as claimed in claim 30, in which the at least one surfactant is present in a concentration of 0.1–10000 μg/ml.

50. The formulation as claimed in claim 49, in which the surfactant is present in a concentration of 1–1000 μg/ml.

51. The formulation as claimed in claim 30, in which the surfactant and/or isotonicizing agent comprises at least one of glycerol and mannitol in a concentration of 100–250 mM.

52. The formulation as claimed in claim 51, further comprising chloride as a buffer substance and/or isotonicizing agent in a concentration of up to 150 mM.

53. The formulation as claimed in claim 30, in which a buffer substance is present in a concentration of 5–250 mM.

54. A process for the production of the formulation as claimed in claim 30, wherein the components are mixed together in the form of aqueous solutions, the pH is adjusted to a desired level, and the mixture is made up to the final volume with water.

55. The formulation of claim 30 wherein the surfactant comprises polysorbate 20, and the formulation further comprises cresol, trometamol and NaCl.

56. An aqueous liquid formulation obtainable by the process as claimed in claim 54.

57. A method of treating diabetes mellitus comprising administering the formulation as claimed in claim 30 to a patient in need thereof.

58. The formulation of claim 30 further comprising at least one insulin, insulin derivative, or active insulin metabolite.

* * * * *

UNITED STATES PATENT AND TRADEMARK OFFICE
CERTIFICATE OF CORRECTION

PATENT NO. : 7,205,276 B2
APPLICATION NO. : 11/007154
DATED : April 17, 2007
INVENTOR(S) : Peter Boderke It is certified that error appears in the above-identified patent and that said Letters Patent is hereby corrected as shown below:

On the title page, item (73), "Gmb," should read --GmbH,--.

In claim 20, column 12, line 60, "1,in" should read --1, in--.

In claim 46, column 14, line 22, "B30-N-myristoyl-Thr$^{829}$Lys$^{830}$" should read -- B30-N-myristoyl-Thr$^{B29}$Lys$^{B30}$--.

Signed and Sealed this

Third Day of July, 2007

JON W. DUDAS
*Director of the United States Patent and Trademark Office*